(12) United States Patent  (10) Patent No.: US 6,632,681 B1
Chu  (45) Date of Patent: Oct. 14, 2003

(54) REAGENT DELIVERY DEVICE AND METHOD OF USE

(75) Inventor: Albert E. Chu, Hillsborough, CA (US)

(73) Assignee: EY Laboratories, San Mateo, CA (US)

( * ) Notice: Subject to any disclaimer, the term of this patent is extended or adjusted under 35 U.S.C. 154(b) by 0 days.

(21) Appl. No.: 09/624,261

(22) Filed: Jul. 24, 2000

(51) Int. Cl.$^7$ ............................................. G01N 1/38
(52) U.S. Cl. .................. 436/178; 436/165; 436/166; 436/177; 436/179; 436/180; 436/808; 436/810; 422/56; 422/58; 422/61; 422/100; 422/101; 422/102; 435/7.1; 435/287.6; 435/287.7; 435/287.8; 435/288.1
(58) Field of Search ................................ 436/177, 178, 436/179, 180, 165, 166, 808, 810; 422/56, 58, 61, 100, 101, 102; 435/7.1, 287.6, 287.7, 287.8, 288.1

(56) References Cited

U.S. PATENT DOCUMENTS

| | | | |
|---|---|---|---|
| 3,248,017 A | 4/1966 | Allen | 222/189 |
| 3,285,296 A | 11/1966 | Ishimaru et al. | 141/26 |
| 3,463,322 A | * 8/1969 | Gerarde | 210/455 |
| 4,376,110 A | 3/1983 | David et al. | 436/513 |
| 4,811,866 A | 3/1989 | Golias | 222/189 |
| 4,978,504 A | * 12/1990 | Nason | |
| 5,006,464 A | 4/1991 | Chu et al. | 435/7.1 |
| 5,056,689 A | 10/1991 | Heyl et al. | 222/189 |
| 5,105,993 A | 4/1992 | La Haye et al. | 222/189 |
| 5,265,770 A | 11/1993 | Matkovich et al. | 222/189 |
| 5,588,559 A | 12/1996 | Vallet mas et al. | 222/92 |
| 5,616,242 A | 4/1997 | Mandola | 210/238 |
| 5,679,535 A | 10/1997 | Joyce et al. | 435/7.9 |
| 5,750,333 A | * 5/1998 | Clark | 435/5 |
| 5,788,124 A | 8/1998 | Bougamont et al. | 222/207 |
| 5,879,635 A | * 3/1999 | Nason | |
| 5,885,526 A | 3/1999 | Chu | 422/56 |
| 5,914,045 A | 6/1999 | Palmer et al. | 210/694 |
| 5,919,365 A | 7/1999 | Collette | 210/419 |
| 5,927,559 A | 7/1999 | Bommer et al. | 222/189.09 |

* cited by examiner

Primary Examiner—Jan Ludlow
(74) Attorney, Agent, or Firm—David J. Brezner; Dorsey & Whitney LLP

(57) ABSTRACT

A device and method for filtering a biologically derived sample and for mixing the sample with a reagent, comprising a fluid container defining a reservoir compartment and including a container outlet, a filter and a fluid flow-through matrix disposed in a flow path between the reservoir compartment and the container outlet. Water-soluble, dried reagent is retained on the matrix. Means is provided for urging sample in an aqueous liquid in the reservoir compartment through the filter and matrix and out the container outlet. Pressure is applied to the sample in an aqueous liquid in the reservoir compartment to cause the sample to flow in liquid through the filter and matrix and out of the container for analysis.

5 Claims, 2 Drawing Sheets

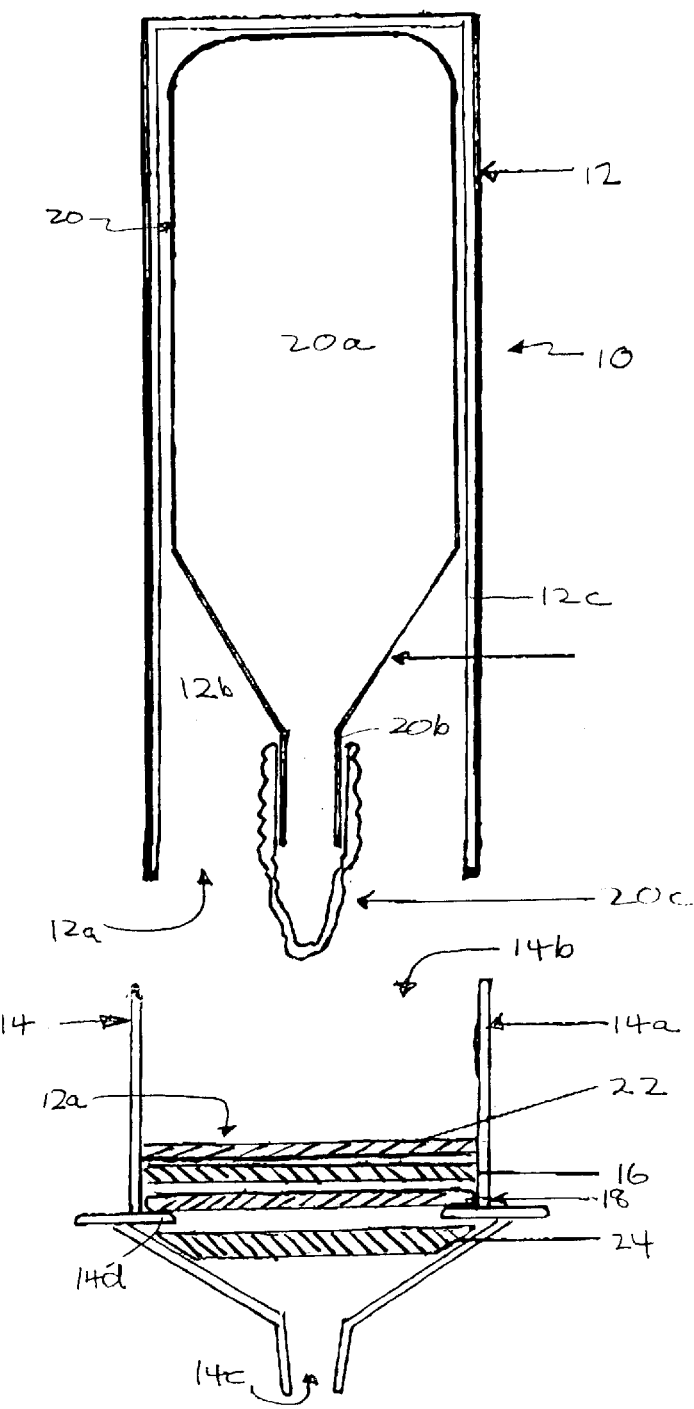
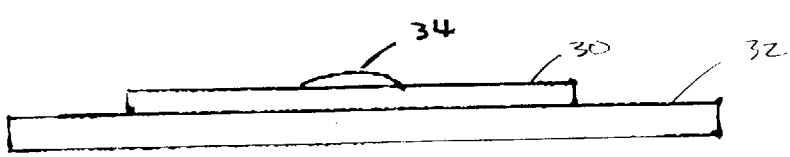
FIG. 2

REAGENT DELIVERY DEVICE AND METHOD OF USE

BACKGROUND OF THE INVENTION

The present invention relates to a method and device for filtering a biologically derived sample and mixing the sample with a reagent for analysis of an analyte in the sample. Once the sample has been filtered and mixed with the reagent, it can be analyzed using conventional analytical techniques. The sample typically comprises an analyte in the form of a bindable target substance in a biologically derived liquid sample suspected of containing the substance. Many different forms of analytical devices can be used for analysis of the filtered, reagent-mixed analyte. For example, such devices are described in U.S. Pat. No. 5,885,526, incorporated herein by reference. Many of such devices employ reaction membranes onto which a receptor is immobilized capable of specifically binding to the target substances. Typically, the sample to be tested is added dropwise to the reaction membrane. If the target substance is present in the sample, it will bind to the immobilized receptor. Various methods are used to determine whether the target substance is bound to the receptor, thus indicating its presence in the sample. In one commonly used method, an immunologically reactive binding capable of specifically binding the target substance attached to a detectable label is applied to the membrane. In the device of the foregoing patent, the sample is added to the top of and flows through a reaction membrane to an absorbent material beneath the membrane that draws the sample through the membrane.

In the testing of blood sample solutions, a known device is sold by EY Laboratories, Inc under the name WBT™ includes a fluid container with a generally cylindrical reservoir body with one open end mating with a removable closure form a fluid passageway. The closure is in the form of a conical nose portion. A filter is placed in the nose portion across the fluid passageway. Blood is placed into the reservoir body which is sealed to the closure. Fluid reagent can be added to the reservoir. The reservoir body is flexible so that by compression of it the blood is forced through the filter and out a conical outlet in droplets. A filtering device of the foregoing type is then used to supply the filtered blood sample to an analytical device such as the membrane device set forth above. The reagents used to form the analysis, such as labels retained on a reaction surface, are added to the membrane in a separate step after the sample flows through the membrane. This separate step adds time to the assay and reduces the potential for technician error.

SUMMARY OF THE INVENTION

According to the invention, a device is provided for filtering a biologically derived sample and for mixing the sample with a reagent. The device comprises a fluid container defining a reservoir compartment and including a container outlet, a filter and a fluid flow-through matrix disposed in a flow path between the reservoir compartment and the container outlet. Water-soluble, dried reagent is retained on the matrix. Means is provided for urging sample in an aqueous liquid in the reservoir compartment through the filter and matrix and out the container outlet.

In another aspect of the invention, a method is provided for filtering a biologically derived sample including at least one analyte and mixing the sample with a reagent for analysis of the analyte. The method includes applying pressure to the sample in an aqueous liquid in a reservoir compartment of a container to cause the sample to flow in the liquid through a filter and a matrix in the container. The matrix carries a dried, water-soluble reagent which is dissolved producing a filtered aqueous liquid mixture of the reagent and sample. The filtered mixture flows out of the container, so that one or more analytes in the filtered mixture may be analyzed.

BRIEF DESCRIPTION OF THE DRAWINGS

FIGS. 1 and 2 are schematic cross-sectional views of the mixing and filtering device of the present invention with the reservoir body and closure separated and illustrating a reaction surface.

DETAILED DESCRIPTION OF THE INVENTION

Figure 1:
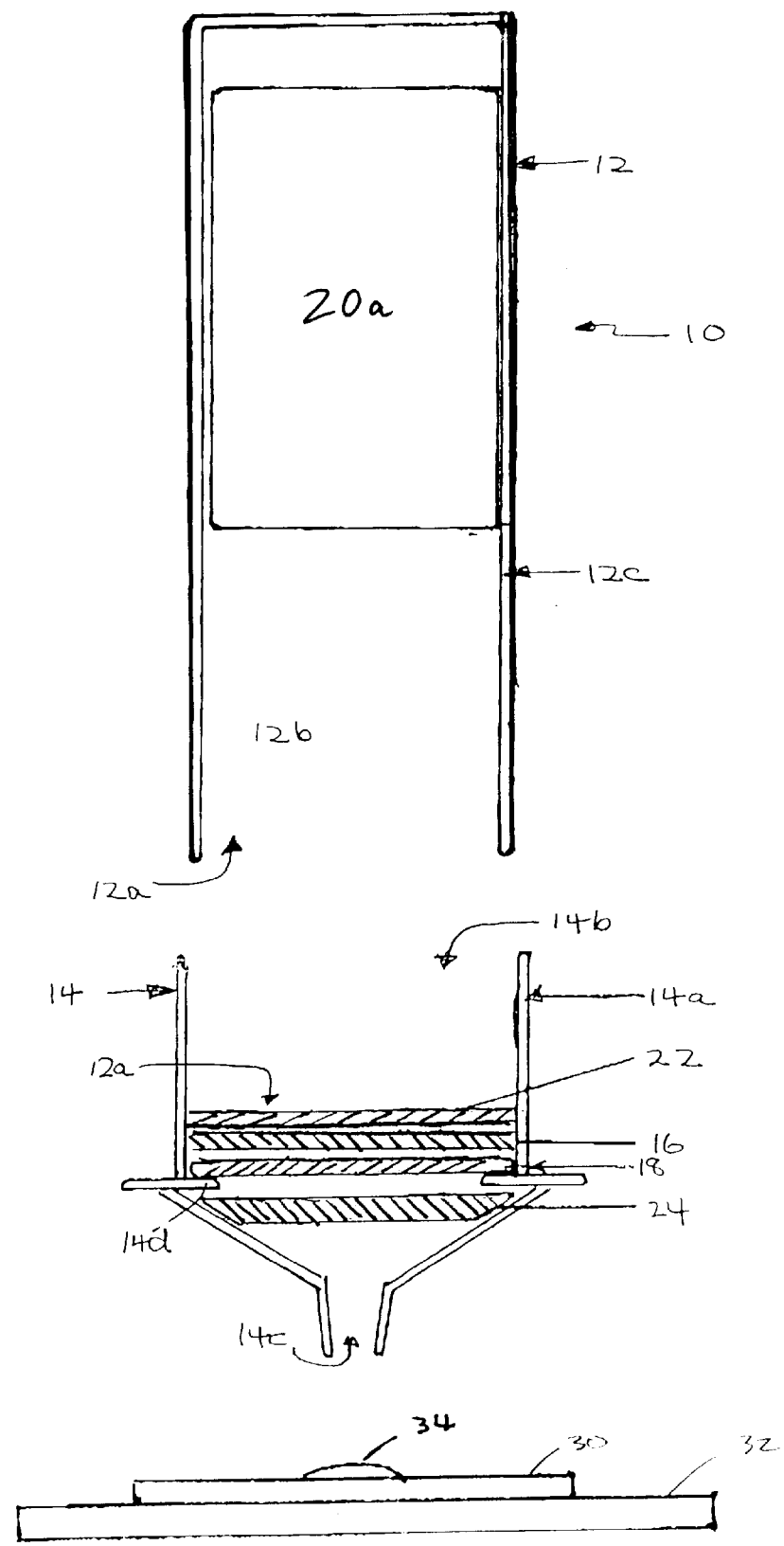

The present invention provides a device for filtering a biologically derived sample and mixing the sample with a reagent which greatly simplifies the analysis of the sample. The biologically derived sample may be analyzed using known analytical procedures. Such samples include bodily fluids such as whole blood, serum, plasma, urine, saliva or the like. In addition, the sample includes extract fluids such as from stool samples, culture of *E. coli*, suspensions from a surface for food safety such as the surface of a chicken or the like, fluids from sewage tested for various purposes, and various cells, bacteria and viruses which are ruptured to release the analyte of interest.

The analytes including a wide variety of proteins such as listed in U.S. Pat. No. 5,006,464 which are conventionally analyzed in immunoassays, as well as other assay systems not categorized as immunoassays which employ the reaction of known binding pairs. In addition, the system is applicable to the analysis of assay systems which are not categorized as immunoassays, e.g., the detection of unknown DNA sequences. The assay device of U.S. Pat. No. 5,006,464 other flow-through assay devices are particularly effective for purposes of the present invention.

Referring to FIG. 1, one embodiment of the filtering and mixing device is illustrated according to the present invention. The device includes a container 10 having a reservoir body 12 defining a body opening 12a at its lowermost end and an internal reservoir 12b. Body 12 includes a generally cylindrical sidewall 12c, preferably made of a flexible material such as plastic, which can be squeezed to urge fluid in the reservoir to filter a matrix and out the container as will be described hereinafter. A suitable plastic material is polyvinylchloride (PVC) or polyethylene or polyester.

The lower wall of reservoir body 12 mates with and forms a seal with removable closure 14. As illustrated, body 12 and closure 14 are separated. Closure 14 includes an upwardly extending cylindrical sidewall 14a dimensioned to form a force-fit seal with the adjacent sidewall of reservoir body 12 which seals against liquid leakage. Other sealing means can be used such as mating screw threads. Closure 14 also includes an opening 14b at its upper end which, with the opening in body 12, forms an internal fluid passageway through container 10. Closure 14 is generally cylindrical at its upper end and generally conical at its lower end and defines an outlet opening 14c dimensioned to cause liquid to exit from container 10 on a drop-by-drop basis when the flexible wall 12 is squeezed to force liquid in reservoir 12b to flow through the filter and matrix, described below, and out opening 14c.

Other ways of urging aqueous liquid in the reservoir compartment through the filter may be employed instead of using a flexible sidewall 12. For example, a piston may be used at the top of the container. A filter 16, suitably in the form of a circular disk, is disposed across the flow path between reservoir body 12 and opening 14c so that liquid in reservoir 12b flows through the filter to retain debris in the liquid which could otherwise interfere with the assay. For example, for the analysis of blood, particulate matter can be filtered by the filter. Suitable filters include membranes made of paper-backed nitrocellulose, polycarbon, nylons, polyester or other porous polymers or other materials. Suitable filter porosities for blood are from about 0.2 to 1.0 micron. Other porosities may be employed depending upon the sample and the desired application. The thickness of the filter is typically about 0.5 mm to 1.5 mm or less, depending on manufacturer specifications. Suitable filters used in the WBT device for filtering blood may be employed for purposes of the present invention (e.g., ones made by Schleicher & Schuell, Millipore or MDI). As illustrated, closure 14 includes a shoulder 14d which projects inwardly of the closure to form a support for the outer periphery of filter 16.

When container 10 is used for whole blood or serum, plasma, urine, saliva or other secretions with particulate matter, the filter is chosen to filter off debris, dirt, cell ghost of red blood cell or white blood cells, sediment or the like in the sample.

In the embodiment of FIG. 1, a matrix 18 is illustrated on the outlet side of closure 14 from filter 16. A water-soluble, dried reagent used in the subsequent analysis of the sample analyte is immobilized on the matrix. The dried reagent is solubilized by the liquid forced through the matrix preferably by application of pressure against the flexible wall of reservoir body 12.

Matrix 18 can be formed of any material which can be placed in the container on which a dried reagent can be immobilized for subsequent solubilization on passage of an aqueous liquid through the matrix. Matrix 18 has sufficient porosity to permit liquid to flow through without undue pressure drops. Suitable matrix materials include filter glass, a flow-through screen, a porous membrane, such as nitrocellulose or coated nitrocellulose, or a packed particle bed with means to retain the particle bed such as porous frits.

One or more dried reagents are immobilized on the matrix material. In one embodiment, the reagent is a detectable label such as lyophilized colloidal gold, fluorescent label, enzyme or the like, conjugated to a chemical moiety capable of binding to a biological molecule. Suitable lyophilized gold conjugates are sold by EY Laboratories, Inc. as listed in its catalogs. The label can be conjugated with any material capable of directly or indirectly binding to the analyte in the sample such as in a competitive or sandwich binding assay by well known techniques. Specifically, the biological conjugate portion of the label typically binds to the capture reagent 22 immobilized to the reaction surface 24. Suitable chemical moieties include proteins carbohydrates, and polynucleotides, specifically including antibodies, antigens, DNA, RNA, lectin, biotin, biotinylated specific protein, biotinylated carbohydrate, biotinylated polynucleotides, avidin, anti-sense protein or the like. Other dried reagents may also be retained on matrix 18 which are not conjugated to a label. For example, such other labels include enzymes, fluorescent dye, bioluminescent or chemiluminescent compounds or encapsulated dye such as microsphere containing dye or charcoal or microsphere linked enzymes or dye or colloidal gold. A stabilizing agent may be added to the reagent on matrix 18 such as sucrose, maltose, melibiose, polyethylene glycol or bovine serum albumin or a buffered saline solution, or combinations thereof.

In one method of immobilization, reagent, such as a known concentration of FITC labeled antibody, is deposited on a matrix (e.g., in the form of fiberglass) and is adsorbed onto the matrix. Then the reagent is allowed to air dry on the matrix and a matrix disk is cut out to place into closure 14 for use in the device. The same procedure applies for other reagents such as biological conjugates labeled with colloidal gold, enzyme, biotin, avidin, or the like.

Another procedure for immobilizing the reagent onto matrix 18 is by lyophilization. Here, the matrix (e.g., fiberglass) is immersed into a solution of the reagent which is quickly frozen such as by embedding into a solution of alcohol and dry ice or liquid nitrogen. The frozen membrane in the form of a disk to be placed into the device is placed into a lyophilizer to be freeze dried by well known techniques.

Referring again to FIG. 1, an optional pouch 20 including an aqueous carrier liquid 20a is disposed in reservoir body 12. Pouch 20 is formed of a readily rupturable material such as polyvinylchloride so that, when wall 12c is squeezed, the pouch is ruptured. Such rupturable pouches are commercially available. Typically, carrier liquid 20a is an aqueous buffer solution which mixes with the sample and flows through the filter and matrix and out the outlet opening 14c. The liquid buffer can be of a conventional type well known for use in the subsequent analysis of the sample analyte. The buffer solution also serves to reconstitute the dried reagent on matrix 18 for use in subsequent analysis. Suitable aqueous buffer solution include conventional components such as phosphates, borates or bicarbonates. Also, a surfactant or detergent may be added for the purpose of decreasing viscosity, providing lubrication effect and micel formation. Liquid is preferably at a pH of about 7.0 to 8 or higher or lower depending on the stability of the reagent and the optimum conditions for the binding pair.

In another embodiment illustrated in FIG. 1, an optional filter 22 may be inserted above filter 16 (between reservoir 12b and filter 16) to provide additional filter capability. In this instance, filter 22 can be of the same type as described for the matrix or filter. This may be desirable for samples such as urine which include large amounts of material to be filtered.

In yet another embodiment illustrated in FIG. 1, matrix 18 may be disposed in the reservoir compartment side of a filter which, in turn, is disposed on the outlet side of the matrix 18. One advantage of this setup is to thoroughly mix the dissolved reagent and sample. As illustrated, filters 16 and 22 are disposed above matrix 18 and an additional filter 24 is disposed below matrix 18. A layer such as a filter 24 disposed between the matrix 18 and outlet 14c can serve to further mix the reagents with the sample solution prior to capture by the capture reagent 24 on membrane 22.

All of filters 16, 22 and 24 or one or more of them can be used, depending upon the application.

In another embodiment, not shown, the system does not include the rupturable pouch 20. In this instance, the sample may be a liquid such as blood in which no additional carrier liquid is added to reservoir compartment 12b. Alternatively, the sample may be filled into compartment 12b and a carrier liquid such as the same aqueous buffer solution is mixed with the sample prior to sealing of closure 14 with reservoir body 12.

In another embodiment, not shown, the sample may be deposited as by swabbing onto a surface at the outlet end of reservoir compartment 12b. In this instance, the deposited sample is not in liquid form. Thus, a carrier liquid such as a buffer solution must be added to reservoir compartment 12b. As described above, the carrier liquid can be in pouch 20 or just contained in the reservoir. In the illustrated embodiment, the sample would be deposited on filter 16 prior to filling the container. By squeezing reservoir body 12, the carrier liquid suspends or dissolves the analyte in the deposited sample for flow through the filter 16 and matrix 18 and out outlet 14c.

Referring again to FIG. 1, the sample and reagent flows out of outlet 14c and are directed to a reaction surface 30 of a conventional device 32. One such reaction surface includes an exposed membrane forming reaction surface 30 with an absorbent material below the membrane contained in a plastic housing. The capture reagent 34, which interacts with the sample analyte such as in an immunoassay, is immobilized on reaction surface 30. A suitable capture reagent is an antibody or antigen or other binding reagent (e.g. ones known to capture analytes). The liquid is drawn through the membrane by the absorbent material. A suitable device of this type is described in U.S. Pat. No. 5,885,526, incorporated herein by reference.

The analysis method may be performed in a single step by flowing the solubilized reagent out of outlet 14c and onto the reaction surface. Alternatively, if desired, additional reagents not coming from container 10 may be added to the surface, such as washing solution. As is conventional, the sample analyte binds directly or indirectly to the reaction surface such as by an immunologically reactive pair, by a DNA hybridization pair, a lectin, carbohydrate pair or other molecules in biological systems or molecules designed to bind double stranded RNA.

Referring to FIG. 2, an embodiment of the invention is illustrated which includes an alternative to the rupturable pouch. Like parts will be designated with like numbers for FIGS. 1 and 2. As illustrated in FIG. 2, the pouch includes an outlet dropper 20b opening facing body opening 12a, with a removable closure such as a force-fit flexible cap 20c. At the time of use, cap 20c is removed and closure 14 is sealed with body 12. Liquid in the pouch is squeezed into the reservoir body 12 at the time of the test.

The following examples are provided to illustrate the present invention.

EXAMPLE 1

The following procedure is used to make a reagent immobilized membrane 18 of FIG. 1. A fiber glass disk (e.g. ⅜" diameter) is immersed into the reagent (Protein A colloidal gold label conjugate. A label made by the procedure of U.S. Pat. No. 5,541,059, incorporated herein by reference. In this instance, the reagent solution is 20 nM $OD^{520}$ (wave length 520 nm) colloidal gold labeled Protein A (or a specific immunoglobulin) conjugate solution in 20 nM phosphate buffer pH 7.4 containing 1% BSA. 50 µl of the solution are added to the top of the membrane and is absorbed. A disk is placed into a freeze dryer and freeze dried.

EXAMPLE 2

In Example, a WBT device is used as container 10 is made of plastic with a flexible wall of the reservoir body. The filter is of a paper-backed nitrocellulose type. A disk of the reagent immobilized matrix made in FIG. 1 is placed in closure 14 between filter 16 and outlet 14c.

Reservoir 12b is partially filled with blood. A phosphate buffered saline solution is placed into a rupturable pouch 20. When it is desired to perform the assay, wall 12c is squeezed to rupture pouch 20 so that the buffer solution mixes with the blood and is filtered by filter 16 and passes through matrix 18 to dissolve the colloidal gold labeled reagent. The sample and reagent mixture in an aqueous solution pass through outlet 14c as drops for deposition onto a reaction surface 30 (paper-backed nitrocellulose) for reaction with capture reagent 34 (as described in U.S. Pat. 5,885,526).

EXAMPLE 3

In this instance, a solid sample is tested for a microorganism. A swab is used to scrape sample from chicken skin. Optionally, the sample then is concentrated by depositing the sample on a filter 16 of sufficient porosity to pass the microorganism. Solution in the pouch is released to carry the microorganism through the filter and matrix containing lyophilized colloidal gold labeled anti-*E. coli* 0157.H7 specific antibody. A red color in the subsequent analysis shows a positive test.

What is claimed is:

1. A method for filtering a biologically derived sample including at least one analyte and mixing said sample with a reagent for analysis of said analyte using a device comprising a fluid container defining a reservoir compartment including a flexible wall portion defining an opening and including a container outlet, a filter and a fluid flow-through matrix disposed in a flow path between said reservoir compartment and said container outlet, water-soluble, dried reagent retained on said matrix comprising a labeled chemical moiety capable of binding to the analyte in said sample, and said container further comprising a removable closure defining said container outlet at one end and defining an opening at its other end mating with said reservoir opening to define therebetween a flow-through passage, said filter and matrix being disposed in said closure, said method comprising (a) depositing said sample onto said filter while said removable closure is detached from said reservoir compartment, (b) connecting said reservoir compartment and closure with a solvent for said sample analyte in said reservoir compartment, (c) applying pressure to said solvent by squeezing said flexible wall portion to cause said sample analyte on said filter to be dissolved in said solution to flow in an uninterrupted continuous liquid stream through said filter and said fluid flow-through matrix in said container, thereby dissolving said reagent and producing a filtered aqueous liquid mixture comprising said reagent bound to said sample analyte, (d) flowing said filtered mixture out of said container to a capture reagent immobilized on a reaction surface to capture said bound reagent analyte, and (e) detecting said label on said captured bound reagent-analyte.

2. The method of claim 1 in which said sample comprises whole blood, serum, plasma, urine or saliva.

3. The method of claim 1 in which said sample flows through said filter in an aqueous carrier liquid.

4. The method of claim 1 in which a carrier liquid is supplied to said container in a rupturable pouch which is ruptured under said applied pressure.

5. The method of claim 1 in which said sample comprises whole blood, serum, plasma, urine or saliva.

* * * * *